United States Patent [19]

Preikschat et al.

[11] Patent Number: 4,871,251

[45] Date of Patent: Oct. 3, 1989

[54] APPARATUS AND METHOD FOR PARTICLE ANALYSIS

[76] Inventors: Fritz K. Preikschat, 16020 Lake Hills Blvd., Bellevue, Wash. 98008; Ekhard Preikschat, 9048 N.E. 41st Street, Bellevue, Wash. 98004

[21] Appl. No.: 119,797

[22] Filed: Nov. 12, 1987

Related U.S. Application Data

[63] Continuation-in-part of Ser. No. 43,223, Apr. 27, 1987, abandoned, which is a continuation-in-part of Ser. No. 821,781, Jan. 23, 1986, abandoned.

[51] Int. Cl.$^4$ .......................................... G01N 15/02
[52] U.S. Cl. ..................................... 356/336; 356/342; 377/11
[58] Field of Search ....................... 356/335, 336, 342; 377/11

[56] References Cited

U.S. PATENT DOCUMENTS

| | | | |
|---|---|---|---|
| 3,676,647 | 7/1972 | Staffin et al. | 377/11 |
| 3,858,851 | 1/1975 | Ogle | 356/336 |
| 3,941,477 | 3/1976 | Schodl | 356/342 |
| 3,998,552 | 12/1976 | Stewart et al. | 356/342 |
| 4,140,395 | 2/1979 | Kveikebaum | 356/336 |
| 4,387,993 | 6/1983 | Adrian | 356/336 |
| 4,492,467 | 1/1985 | Drain et al. | 356/336 |

FOREIGN PATENT DOCUMENTS 1919628 8/1974 Fed. Rep. of Germany .
1305923 2/1973 United Kingdom .

OTHER PUBLICATIONS

Preining, O., Wagner, P., Pohl, F. and Szymanski, W., Heterogeneous Nucleation and Droplet Growth, Part III of Aerosol Research at the Institute for Experimental Physics of the University of Vienna, pp. 127-135 (Feb. 1981).
Diehl, S., Smith, D.T., and Sydor, M., "Analysis of Suspended Solids by Single-Particle Scattering", Applied Optics, vol. 18, no. 10, pp. 1653-1658.

*Primary Examiner*—Richard A. Rosenberger
*Attorney, Agent, or Firm*—Christensen, O'Connor, Johnson & Kindness

[57] ABSTRACT

Apparatus for analyzing particles contained in a fluent edium (12). The apparatus includes a body (20) having a window (30), an optical source preferably comprising a laser diode (100) having a small light emitting area (140), and an optical system (102) for focusing the light from the laser diode at a focal spot (84) such that the size of the focal spot is approximately equal to the size of the light emitting area of the laser diode. A photodetector (106) is mounted in the body and detects light backscattered from the focal spot by particles in the fluent medium, and produces an electrical signal that comprises a series of pulses associated with the particles. The electrical signal is input to a detector that counts the pulses and indicates the number of particles in the fluent medium. The detector includes discrimination means for preventing the counting of a pulse that has a rise or fall time above a predetermined threshold, thereby discriminating against particles that are not at the focal spot. Means are provided for measuring the integrated amplitude of the electrical signal, and for varying the distance between the focal spot and the window to maximize such integrated amplitude. An intrinsically safe embodiment is also disclosed in which the probe positioned at the measuring site does not include any electrical components. This embodiment may be implemented using light of multiple wavelengths for characterizing individual particles.

29 Claims, 11 Drawing Sheets

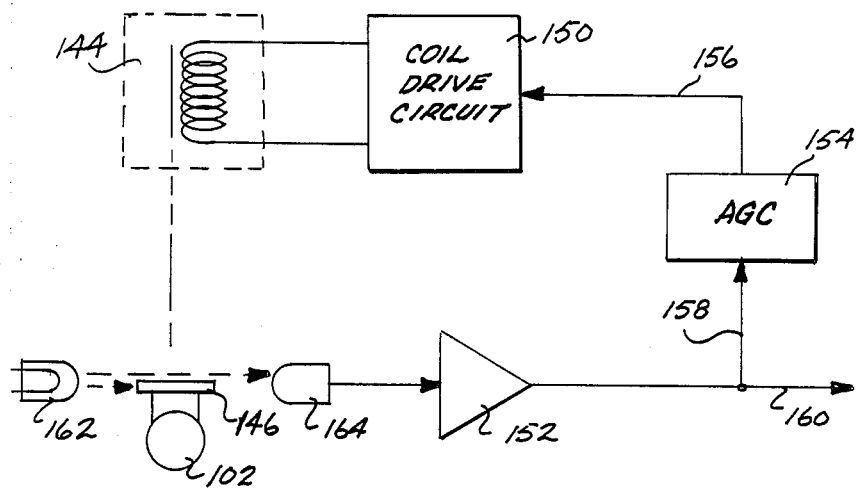
Fig. 4.
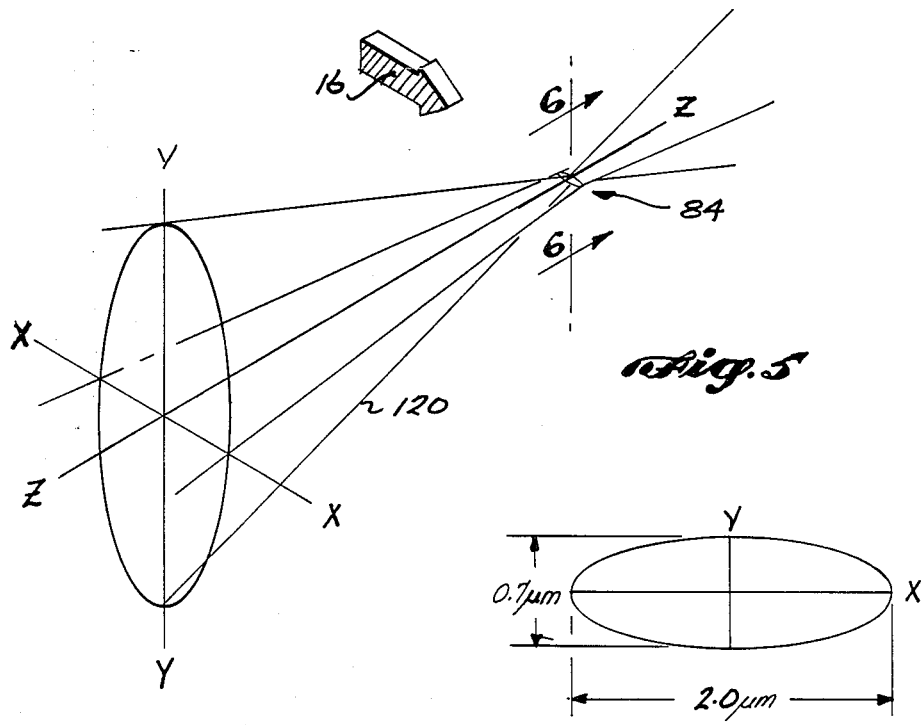
Fig. 5
Fig. 6

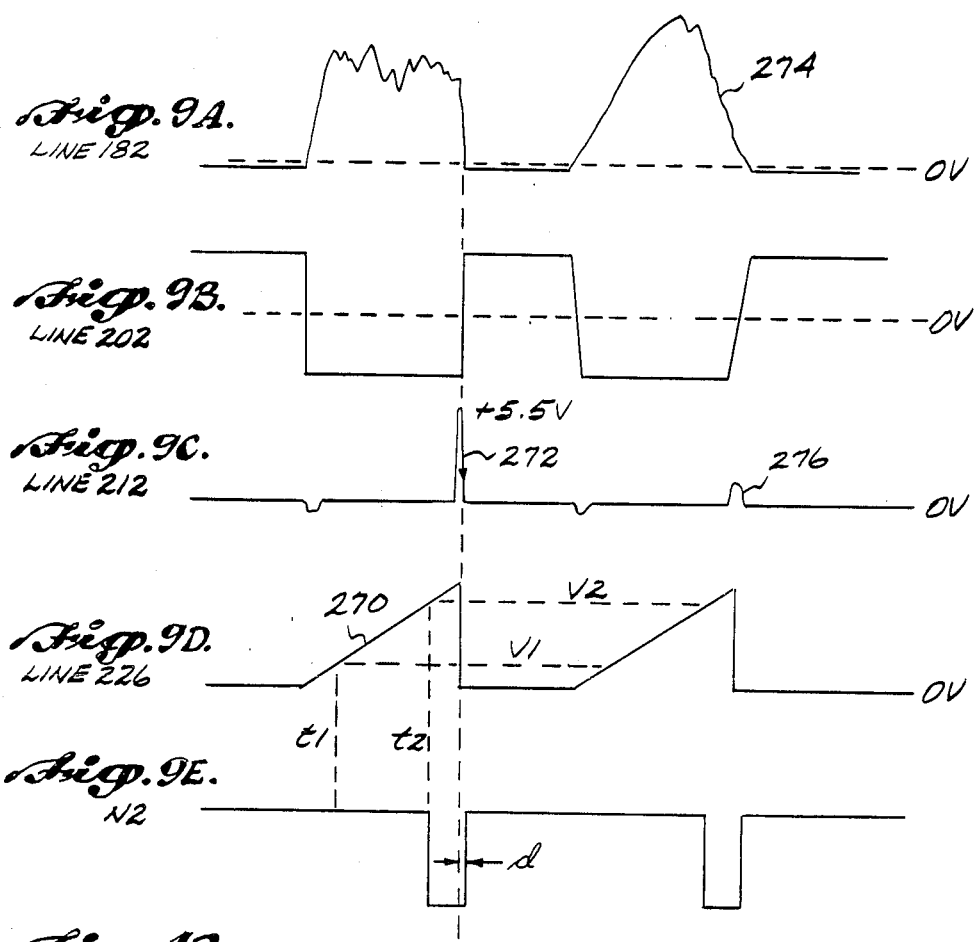

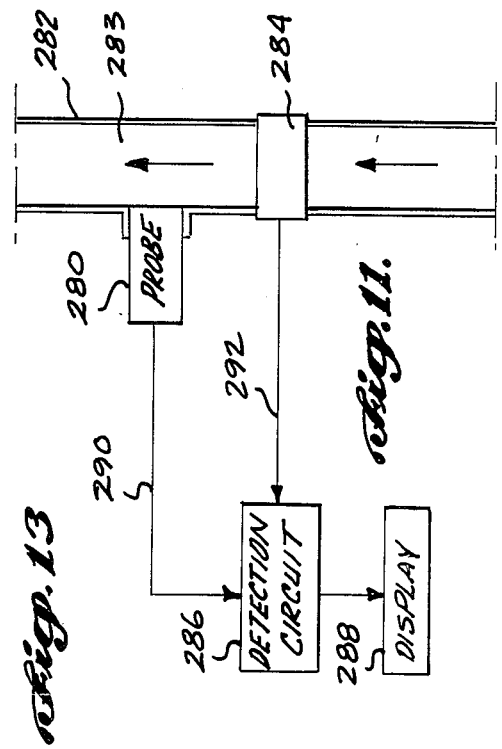
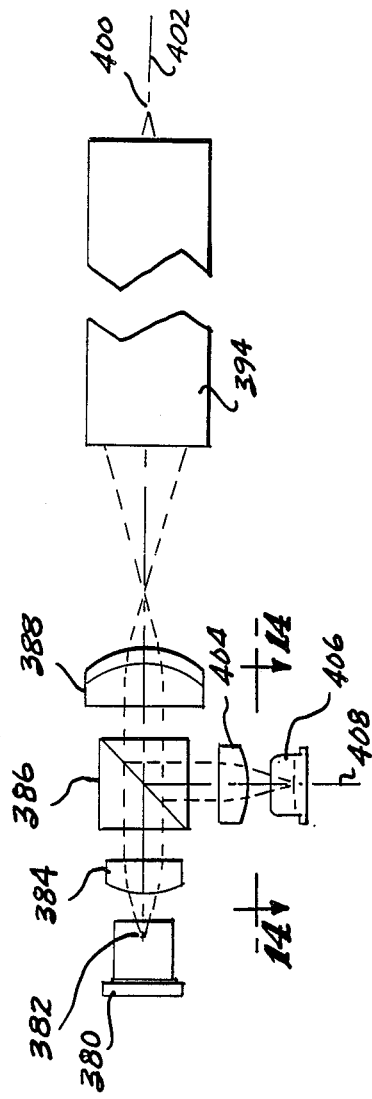
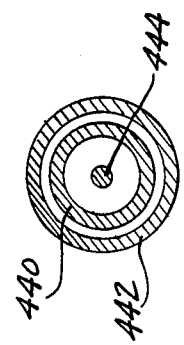

APPARATUS AND METHOD FOR PARTICLE ANALYSIS

This application is a continuation-in-part of U.S. Ser. No. 043,223, filed Apr. 27, 1987, now abandoned, which is in turn a continuation-in-part of U.S. Ser. No. 821,781, filed Jan. 23, 1986, now abandoned.

FIELD OF THE INVENTION

The present invention relates to an apparatus and method for analyzing the size and number of particles in a fluent medium.

BACKGROUND OF THE INVENTION

There exist many applications in industry and science in which it is required to determine the size and number of particles suspended in a fluent (i.e., liquid or gaseous) medium. These determinations can be very important in many manufacturing processes such as pharmaceuticals, plastics, chemicals, and paper, to name a few examples. Processes such as crystal growth, precipitation, polymerization, gravimetric separation, grinding, etc., must be monitored to control the quality of the product.

The particles in a slurry can range from submicron to millimeters in size, and the relative quantities of the different sizes may be very critical to the quality and performance of the product. For example, a pulp slurry may contain fibers which are about 10–40 microns in size as well as brightener and filler particles (clay) which are mostly less than 4 microns in diameter. The size of coal dust will influence the rate at which it burns. The powders in pills and capsules must be ground to specific sizes to dispense drugs at optimum rates in the human body.

Ideally, the particle measurements should be made on-line to provide realtime information for process control, and also avoid distortion of the particle size information by removing samples from the process.

In the past, a number of different technologies have been developed for the analysis of particle size, using conventional or laser light sources, ultrasonic beams, cathode ray tubes, and Stoke's law of sedimentation rates. The optical devices which exist today utilize transmission geometries and use various methods to determine size. The method used in most commercially available instruments measures the light intensity scattered at various small forward angles (e.g., Fraunhoffer diffraction patterns) to determine particle size. Another method uses a beam of light scanned scross a small chamber through which the fluent medium is force to flow. A detector is positioned on the opposite side of the flow such that particles cause interruptions of the light received by the detector (Staffin, U.S. Pat. No. 3,676,647, and Ogle, U.S. Pat. No. 3,858,851). The time that the beam is interrupted is used as a measure of the size of the particle. A variation on this method is devices which force the particles through a sampling chamber at a known velocity and keep the beam stationary (Eisert, U.S. Pat. No. 4,110,043).

The major reason for the use of the transmission geometry is that the light scattered by particles in the forward direction (i.e., less than 90° from the original direction of the light beam) is up to 10,000 times more intense than the light scattered in the backwards direction. The limitation of transmission systems is that the particle concentration in the medium must be very low (less than 0.01 percent by volume) to allow the light to pass through the fluent medium, be scattered by a particle, and then pass further through the medium to be detected. Obviously, the use of such methods is impossible, at normal process concentrations, which are commonly much greater than one percent. Attempts to use such devices on-line must involve sampling systems which are susceptible to clogging, and dilution systems that cause errors by altering the composition of the sample.

SUMMARY OF THE INVENTION

The amount of light scattered by a fluent medium depends on a number of parameters: the number of particles suspended in the medium, the index of refraction of both the particles and the fluent medium, the size and shape of the particles, and the turbidity and color of the medium. With an unfocused light beam one is able to measure only the sum total of all of these effects, i.e., if one wants to measure one parameter only, e.g., particle size, one has to assume that all of the other parameters remain constant. In this regard, devices which measure particle size on a macroscopic basis by illuminating a large area (Kreikebaum, U.S. Pat. No. 4,140,395) to determine the integrated scattering from a suspension of particles will be directly dependent on turbidity and optical density. Such devices can thus only measure the mean particle size, and only if the other variables remain constant.

The present invention provides an optical technique for analyzing individual particles on a microscopic basis suspended in a fluent medium. The term "particles" as used herein includes cellular particles such as bacteria, and in general encompasses any material having optical properties different from that of the suspending fluent medium. The technique of the present invention is based upon the backscattering of light by the particles, and does not require that the fluent medium flow through a sample chamber. Given presently available optical technology, the technique of the present invention is capable of detecting particles as small as 0.5 microns in diameter.

It is important to note that because of the extremely small amounts of light backscattered by individual particles (up to 10,000 times less than at forward angles), the backscattering method has never before been used to measure the particle size of individual particles. Only by the use of a focused beam can the size of individual particles be measured with backscattered (scattering angle greater than 90°) light.

The present invention is based upon the recognition that if the total power of the light source is concentrated into a diffraction-limited focal spot of comparable size to the smallest particles to be measured (about 1 micron), then sufficient light can be backscattered, even by micron-sized particles, to be measured by a sensitive high-speed detection system. The capability of the present invention to measure the size of individual particles at normal process concentrations through a single optical access port eliminates the limitations of the aforementioned devices.

In one preferred embodiment, an apparatus according to the present invention comprises a body that includes a window, illumination means mounted to the body, photodetector means and detection means. The illumination means includes an optical source, an optical system for receiving light from the optical source and focusing the light at a focal spot in the fluent medium and means for adjusting the distance between the focal spot and the window. The photodetector detects pulses of light from the illumination means that is backscattered by particles at the focal spot, and produces a corresponding electrical signal. The detection means receives the electrical signal, and includes size measurement means for measuring the length of time that individual particles are in the focal spot, to thereby provide an indication corresponding to the size of particles in the fluent medium. The detection means further includes means for producing an integrated amplitude signal having a magnitude corresponding to the average amplitude of the electrical signal, such that the distance between the focal spot and window may be adjusted based upon the integrated amplitude signal.

The optical source preferably comprises a laser diode, and the optical system focuses the light from the laser diode such that the size of the focal spot is approximately equal to the size of the light emitting area of the laser diode. The photodetector means provides a series of pulses respectively associated with particles positioned at the focal spot, and the detection means comprises means for counting such pulses, and means for preventing the counting of a pulse that has a rise time above a predetermined threshold. By means of such rise time discrimination, the system does not count particles that are not at the focal spot.

In a further preferred embodiment, the apparatus comprises a probe that may be implemented entirely without electrical components, to thereby provide an intrinsically safe probe particularly suitable for use in explosive or harsh environments. In this embodiment, the illumination means comprises a monomode fiber optic cable having first and second ends, a laser diode, and means for coupling light from the laser diode into the first end of the monomode cable. The optical system is positioned to receive light from the second end of the monomode cable. Light backscattered by particles at the focal spot may be returned from the probe by a return fiber optic cable, and pneumatic means may be provided for causing the focal spot to oscillate in the fluent medium. For this embodiment, means may also be provided for synchronizing the detection means to the oscillation of the focal spot. A multiple wavelength system for characterizing individual particles is also disclosed.

BRIEF DESCRIPTION OF THE DRAWINGS

FIG. 4 is an electrical schematic diagram of the vibration system;

FIG. 5 is a graphical view of the beam and focal spot;

FIG. 6 is a cross-sectional view taken along line 6—6 of FIG. 5;

FIGS. 9A through 9E are a signal diagrams corresponding to the circuit of FIG. 8;

FIG. 10 is a logic diagram corresponding to the circuit of FIG. 8;

FIG. 11 illustrates the use of a nonscanning probe according to the present invention;

FIG. 13 illustrates the use of a common optical path for the illumination and backscattered light;

FIG. 14 is a cross-sectional view taken along the line 14—14 in FIG. 13, illustrating the use of a target-shaped detector to simultaneously measure backscattered light from the focal spot and the halo;

DETAILED DESCRIPTION OF THE DRAWINGS

Figure 1:
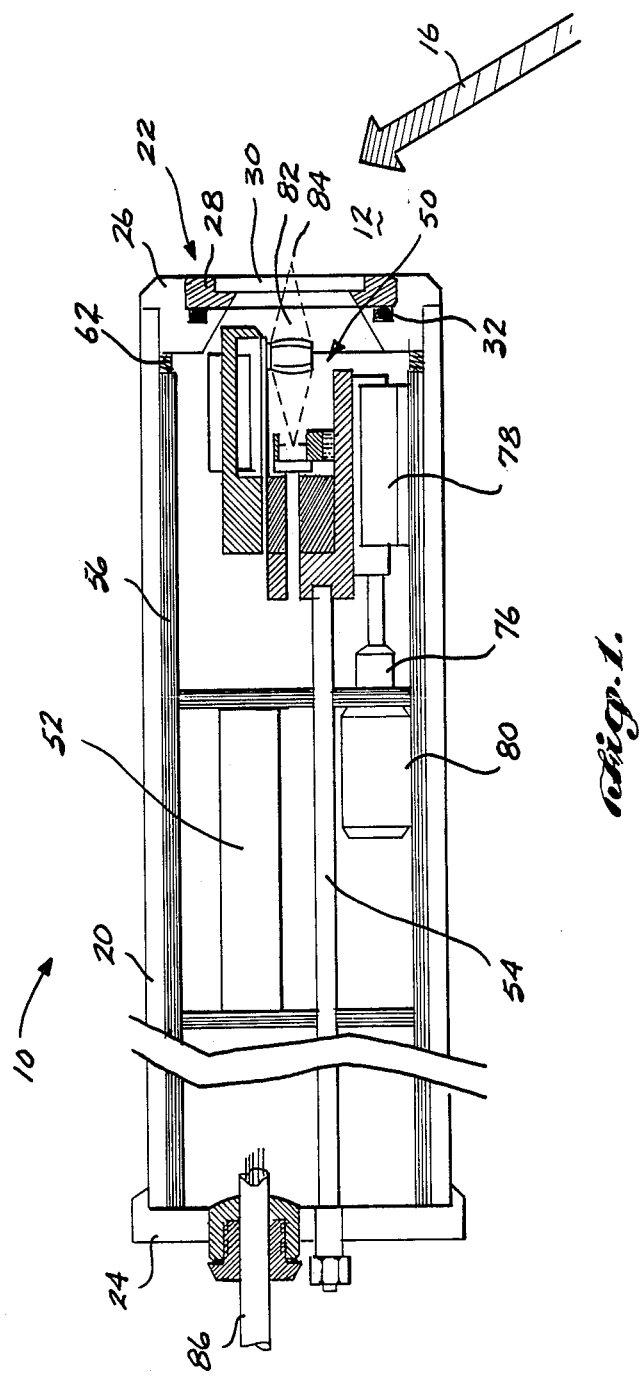
FIG. 1 is a cross-sectional view of a probe according to the present invention for on-line particle measurement.

The principles of the present invention are disclosed by way of example by probe 10 shown in FIG. 1. Probe 10 is adapted for analyzing the sizes and numbers of particles suspended in fluent (e.g., liquid or gaseous) medium 12. Probe 10 comprises cylindrical tube 20 that includes forward end 22 and back end 24. Forward end 22 includes front wall 26 and window carrier 28 in which window 30 is centrally mounted. The window carrier is threaded into front wall 26, and O-ring 32 prevents leakage of the fluent medium into the interior of the probe. The window permits light to pass between the interior of tube 20 and fluent medium 12. For the common case in which the fluent medium flows past the probe, the probe is preferably positioned such that window 30 is oriented at a slight angle to the flow direction (indicated by arrow 16), an arrangement that tends to keep window 30 clean and free of accumulated sediment. In the alternative, forward end 22, including window 30, may be inclined with respect to the longitudinal axis of probe 10. In a preferred embodiment, window 30 comprises synthetic sapphire, and window carrier 28 comprises titanium. The advantages of sapphire are its hardness, abrasion resistance, and low light loss in the infrared. The advantage of titanium is that it is highly corrosion resistant, and can be used over a wide range of pH levels. However, the most important advantage flowing from the combination of sapphire and titanium is that the temperature coefficient of synthetic sapphire (8 parts per million per degree centigrade) is very close to that of titanium (8.5 parts per million per degree centigrade). Thus the window/carrier combination can be heated over a wide range of temperatures, without cracking the window.

Enclosed with tube 20 are optical assembly 50, electronics package 52, heat pipe 54 and insulating inner tube 56. Inner tube 56 is positioned adjacent the inner wall of tube 20, and is longitudinally secured by means of back end 24 and springs 62 at forward end 22 of the tube. The inner tube serves to thermally insulate the optical assembly and the electronics package, for those applications in which the cylindrical sidewalls of mounting tube 20 are inserted into the fluent medium. Optical assembly 50 is mounted within tube 20 adjacent window 30 by bearing slide 78 that permits the optical assembly to be moved along the longitudinal probe axis by stepper motor 80 and positioner 76. The optical assembly generates light beam 82 and focuses the light beam at focal spot 84 that is positioned just outside window 30. As described in greater detail below, the optical assembly also includes means for causing focal spot 84 to vibrate parallel to window 30, and means for detecting light backscattered by particles suspended in the volume of fluent medium 12 at the focal spot.

Heat pipe 54 extends rearwardly from the optical assembly to back end 24 of tube 20. The heat pipe conducts excess heat away from the optical assembly. Electronics package 52 is connected by suitable electrical conductors (not shown) to the optical assembly, and to coaxial cable 86 that extends from back end 24. Coaxial cable 86 serves to connect probe 10 to a suitable detection circuit, as described below.

It is to be understood that the present invention is not limited to the specific arrangement shown in FIG. 1. For example for some applications, the probe may be contained within the fluent medium. In other applications, the optical assembly may be positioned adjacent a glass container or conduit that contains the fluent medium or through which the fluent medium is either stationary, or is being stirred to produce a circular flow. This versatility is a significant advantage of the present invention, and derives in significant part from the fact that the present invention uses a backscattering rather than transmission detection method, and does not require the fluent medium to flow through a sample chamber.

Figure 2:
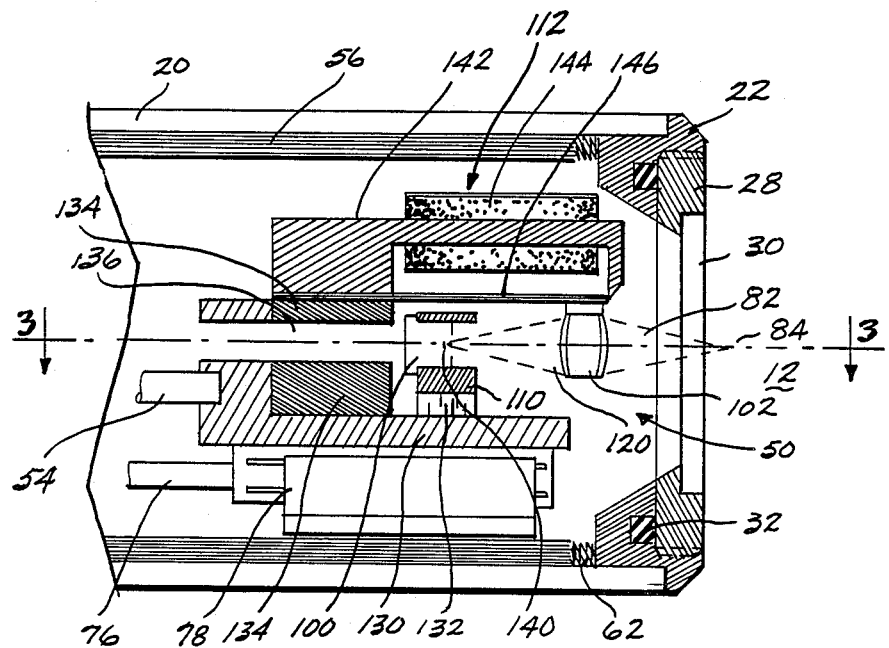
FIG. 2 is a cross-sectional view of the optical assembly of the probe of FIG. 1.
Figure 3:
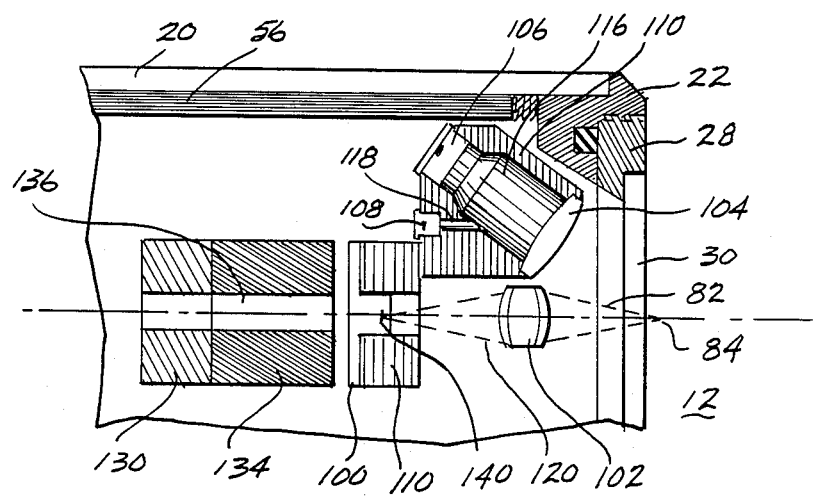
FIG. 3 is a cross-sectional view taken along line 3—3 of FIG. 2.

A preferred embodiment of optical assembly 50 is shown in greater detail in FIGS. 2 and 3. The optical assembly includes laser diode 100, lens system 102, lens 104, and photodetectors 106 and 108. Laser diode 100, lens 104 and photodetectors 106 and 108 are supported in aluminum block 110. Lens system 102 is supported by vibration assembly 112, as described more fully below. Block 110 includes passages 116 and 118 through which light passing through lens 104 may reach photodetectors 106 and 108. In operation of the system, laser diode 100 emits beam 120 that is focused by lens system 102 to produce beam 82 focused on focal spot 84. Particles in fluent medium 12 at focal spot 84 backscatter some of the light of beam 82, and a portion of the backscattered light is collected by lens 104 and focused at photodetector 106. Photodetector 108 is an optical element of the optical assembly, and may be included to detect the ambient light level in fluent medium 12 (via lens 104) away from focal spot 84. Lens 104 is also an optical element, and may be omitted if photodetector 106 is sensitive enough to detect unfocused light scattered from focal spot 84.

Laser diode 100 produces monochromatic beam 120 that is generated from radiating area 140 of the laser diode. The optical assembly includes laser diode 100, lens system 102, lens 104, and photodetectors 106 and 108. Laser diode 100, lens 104 and photodetectors 106 and 108 are supported in aluminum block 110. Lens system 102 is supported by vibration assembly 112, as described more fully below. Block 110 includes passages 116 and 118 through which light passing through lens 104 may reach photodetectors 106 and 108. In operation of the system, laser diode 100 emits beam 120 that is focused by lens system 102 to produce beam 82 focused to focal spot 84. Particles in fluent medium 12 at focal spot 84 backscatter some of the light of beam 82, and a portion of the backscattered light is collected by lens 104 and focused at photodetector 106. Photodetector 108 is an optical element of the optical assembly, and may be included to detect the ambient light level in fluent medium 12 (via lens 104) away from focal spot 84. Lens 104 is also an optional element, and may be omitted if photodetector 106 is sensitive enough to detect unfocused light scattered from focal spot 84.

Laser diode 100 produces monochromatic beam 120 that is generated from radiating area 140 of the laser diode. Typical dimensions for radiating area 140 for currently available laser diodes are 0.7 by 2.0 microns. A suitable component for laser diode 100 is the type ML 4102 laser diode available from Mitsubishi. These very small dimensions are taken advantage of in the present invention by providing lens system 102 that focuses beam 120 to a focal spot 84 having dimensions comparable to the dimensions of radiating area 140, without the use of spatial filtering or complex optics. In order to provide for such focusing, lens system 102 is positioned at a distance of $2f$ from radiating area 140, where f is the focal length of lens system 102. This arrangement produces an image of the radiating area at focal spot 84 at a distance of $2f$ from the lens system. Lens system 120 is preferably a triplet lens system, as shown in FIGS. 1-3, in order to eliminate geometric aberration in beam 82. Because beam 120 is monochromatic, chromatic aberration is not a factor. In a preferred embodiment, lens system 102 has a focal length of 7.5 millimeters, and the lens system is positioned 15 millimeters from the radiating area 140, thus producing a focal spot 84 that is spaced 15 millimeters from lens system 102. The position of focal spot 84 with respect to window 30 is discussed in detail below.

The laser diode 100 and block 110 are mounted to base 130 and plastic block 134. If the ambient conditions require, a thermoelectric cooling element 132 may be used between block 110 and base 130 to establish a temperature gradient between these elements so as to maintain the laser diode at a suitable operating temperature. Base 130 is in thermal contact with heat pipe 54 to conduct heat away from the optical assembly. The base is mounted to the movable part of bearing slide 78 which is in turn attached to positioner 76. The fixed part of bearing slide 78 is mounted to inner tube 56. The bearing slide, positioner, and stepper motor provide means to adjust the distance between window 30 and focal spot 84. Block 134 is mounted to base 130 and provides support and vibration isolation for vibration assembly 112. Passage 136 is provided for electrical connections to laser diode 100.

In a preferred embodiment, lens 104 has a focal length of 8 millimeters and a diameter of 10 millimeters. The lens focuses the light scattered by particles at focal spot 84 onto photodetector 106 that is mounted a distance of $2f$ (16 millimeters) behind lens 104. Photodetector 106 has a large sensing area (2.5 millimeters in diameter), so that the photodetector will capture light scattered from focal spot 84, even when the focal spot is scanned over a distance of several millimeters. The orientation of lens 104 and photodetector 106 ensures that light reflected from window 30 will not be received by the photodetector.

Vibration assembly 112 comprises mild steel support 142, coil 144, and leaf spring 146. The entire vibration assembly is mounted to block 134. Energization of coil 144 by a suitable AC signal causes leaf spring 146 and attached lens system 102 to vibrate towards and away from coil 144, in an up and down direction in FIG. 2. This vibration will cause focal spot 84 to vibrate parallel to window 30, in a direction into and out of the drawing in FIG. 3. Thus focal spot 84 will sweep through and sequentially illuminate an essentially linear volume of fluent material 12, and reflections from particles in such volume will be detected by photodetector 106 and processed as described below. A suitable vibration frequency for lens system 102 and focal spot 84 if 500 Hertz, with a peak-to-peak displacement of the focal spot of 2 millimeters.

Coil 144 may be driven by the servo system illustrated in FIG. 4. The servo system comprises coil drive circuit 150, LED 162, photodiode 164, amplifier 152 and AGC (automatic gain control) circuit 154. More or less light from LED 162 is received by photodiode 164 as leaf spring 146 moves down and up, causing the current to amplifier 152 to be reduced or increased. Coil drive circuit 150 energizes coil 144 at an amplitude controlled by AGC circuit 154 via a signal on line 156. AGC circuit 154 adjusts the signal on line 156 such that the AC amplitude of feedback signal 158 is kept constant. The signal on line 158 represents the position of the spring 146 and therefore of lens 102 and focal point 84, and this signal may be sent to the detection circuit, described below, on line 160. It may be desired to use such a signal to limit the analysis of the pulses from photodiode 106 (FIG. 3) to time periods in which the focal spot is near the center of its range of motion, i.e., to those time periods during which the velocity of the focal spot is constant.

Window 30 may comprise any means by which the light is passed into and out of the fluent medium being analyzed. There may be instances where the process conditions (temperature, pressure, explosive gases) may be such that it is desirable to locate the electronics parts of the optical assembly some distance from the point of measurement. For these applications, alternative optical arrangements may be used, such as fiber optics or periscope optics, as described in detail below.

In the past, optical particle analyzers have typically relied on a transmission geometry rather than a back-scattering or reflection geometry. In an arrangement using transmission geometry, particles are detected as they pass between the optical source and receiver. On the other hand in a backscattering arrangement the detector is positioned to detect light reflected or backscattered by the particles. One of the advantages of the backscattering arrangement of the present invention is that the measurement is not limited by the diffraction effects that come into play when the particle size is comparable to that of the focal spot. A second advantage of the present invention is that it is not necessary to distort the fluent medium being measured by forcing it to flow through a sample chamber as the particles are analyzed.

The geometry of beam 82 and focal spot 84 is illustrated in greater detail in FIGS. 5 and 6. In these FIGS., a coordinate system is used in which the Z axis defines the longitudinal axis of beam 82, and in which the X and Y axes define the beam cross section. As illustrated, beam 82 has a comparatively large cross section in the Y direction and a comparatively small cross section in the X direction. At focal spot 84, the cross section of the beam is as illustrated in FIG. 6, with the focal spot having dimensions corresponding to that of light emitting area 140 of laser diode 100, i.e., a diameter along the X axis of approximately 2 microns and a diameter along the Y axis of approximately 0.7 microns. The direction of movement of focal spot 84 due to the vibration of lens system 102 is in the Y direction, i.e., normal to the long cross-sectional axis of the beam and to the flow direction indicated by arrow 16. In the coordinate system shown in FIGS. 5 and 6, lens 104 and photodetector 106 are located in the X-Z plane.

Figure 7:
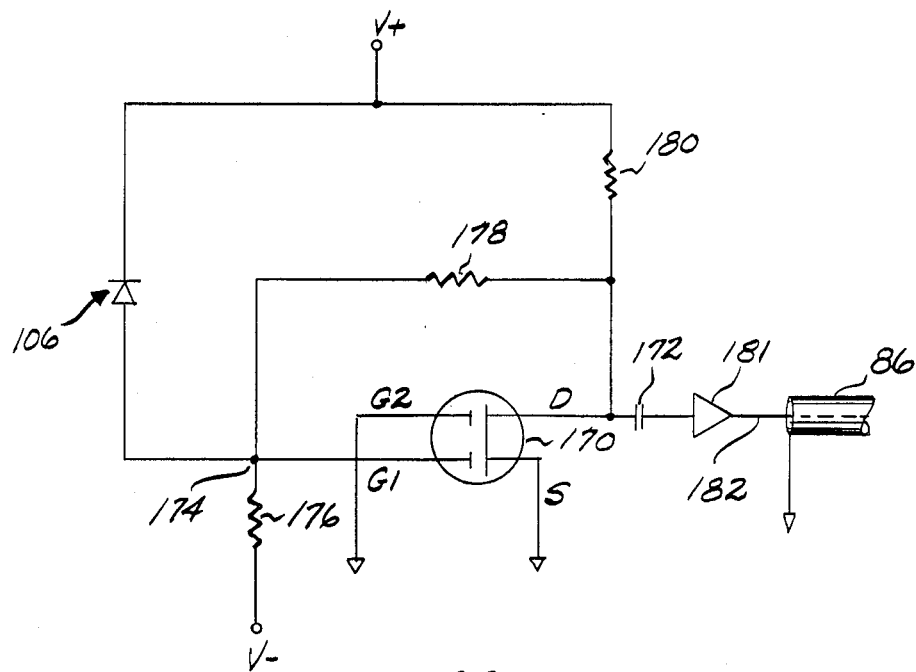
FIG. 7 is a circuit diagram of the preamplifier.

Electronics package 52 (FIG. 1) contains a conventional drive circuit for laser diode 100, and a preamplifier for amplifying the output signal of photodiode 106. A suitable preamplifier circuit is illustrated in FIG. 7. The preamplifier comprises photodiode 106 and dual gate gallium arsenide field effect transistor (GaAsFET) 170. GaAsFET 170 includes gates $G_1$ and $G_2$, drain D and source S. The output of the preamplifier is taken from drain D through capacitor 172 and amplifier 181 into signal line 182 of coaxial cable 86. Gate $G_2$ and source S of GaAsFET 170 are connected to ground potential. The cathode of photodiode 106 is connected to positive voltage supply $V_+$, and the anode of the photodiode is connected to gate $G_1$ via node 174. Node 174 is connected to negative voltage supply $V_-$ via resistor 176, and to drain D via resistor 178. Drain D is connected to positive voltage supply $V_+$ via resistor 180. In the preamplifier in FIG. 7, photodiode 106 is reverse biased, the photocurrent through the photodiode being opposite to the conduction current. Without reverse biasing, the response speed of the photodiode would be slow, due to the high capacity at the diode junction. With a reverse bias, the photodiode capacitance is reduced, and the response speed is correspondingly increased. A suitable component for GaAsFET 170 is the MRF 966 N channel GaAsFET available from Motorola.

The grounding of gate $G_2$ and source S results in a high separation between the input and output stages, i.e., very little feedback and high signal-to-noise ratio. The interface circuit comprising resistors 176 and 178 provides a relatively high input impedance, to provide a good impedance match between photodiode 106 and GaAsFET 170. Resistors 176 and 178 are selected such that node 174 is maintained at a potential of approximately $-1.8$ to $-2.2$ volts. When the current through photodiode 106 goes up in response to the receipt of illumination, the voltage at gate $G_1$ goes up, and the voltage at drain D goes down. The latter voltage is fed back via resistor 178, and maintains the voltage at gate $G_1$ nearly constant at about minus 2 volts, producing a high signal-to-noise ratio. In some applications, it may be desirable to use two GaAsFETs in series to provide a larger degree of amplification of the photodetector signal.

Photodiode 106 detects light, via lens 104, whenever focal spot 84 sweeps past a particle in fluent medium 12, and/or whenever a particle flows through the focal spot, such that the particle scatters some of the light of beam 82 back towards lens 104. At a velocity of two meters per second, a one micron particle will traverse a one micron focal spot in one microsecond. The corresponding backscattered signal will therefore go from zero (or ambient) to its maximum value in a time period on the order of 0.4 microseconds. The preamplifier must be able to respond to such a pulse, and therefore it should be linear up to about two megahertz. Because this frequency is in the braodcast range, the preamplifier circuit should be shielded and located within probe 10 adjacent to the photodetector. The preamplifier circuit is followed by a conventional operational amplifier 181 with a transistor drive circuit to feed the output signal into a 50 ohm coaxial cable 86. A suitable cable is type RG 58 A/U or equivalent. Using such a cable, the output signal from the preamplifier can be transferred over a distance of 100 feet or more into the input of the detection circuit, which may therefore be located in a separate enclosure.

The present invention takes advantage of the way in which the beam is emitted from the laser diode. Referring to FIG. 5., the beam spreads at a full angle of about 33 degrees in the Y-Z plane and about 11 degrees in the X-Z plane. The beam is focused to focal spot 84 at the same angle. The beam intensity decreases rapidly at increasing distance from the focal spot 84, because of the large divergence of the beam. Thus, particles which pass through the beam 82 in front of or behind the focal spot 84 will not scatter the full intensity of the beam as rapidly as particles which pass through the focal spot. The rate-of-increase or "rise-time" of the signal at photodiode 106 in FIG. 3 may therefore be used as a criterion for selecting which particles have passed through the focal spot.

The large solid angle of beam 120 also increases the overall signal-to-noise ratio, because of the diminished beam intensity even at small distances from the focal spot. The large divergence and corresponding convergence angle can be achieved with other laser types only by utilizing bulky and expensive beam expanders and focusing optics. The laser diode can radiate as much or more power as conventional helium-neon lasers (typically 5 milliwatts continuous), and the beam can be expanded and refocused with simple and inexpensive optics, concentrating the full power available at the focal spot. It should be noted that this method can only be used in a backscattering geometry, or else the fluent medium must be forced through a very small passage through which only a few particles could pass at the same time, which would severely limit the usefulness of the device as described above.

Figure 8:
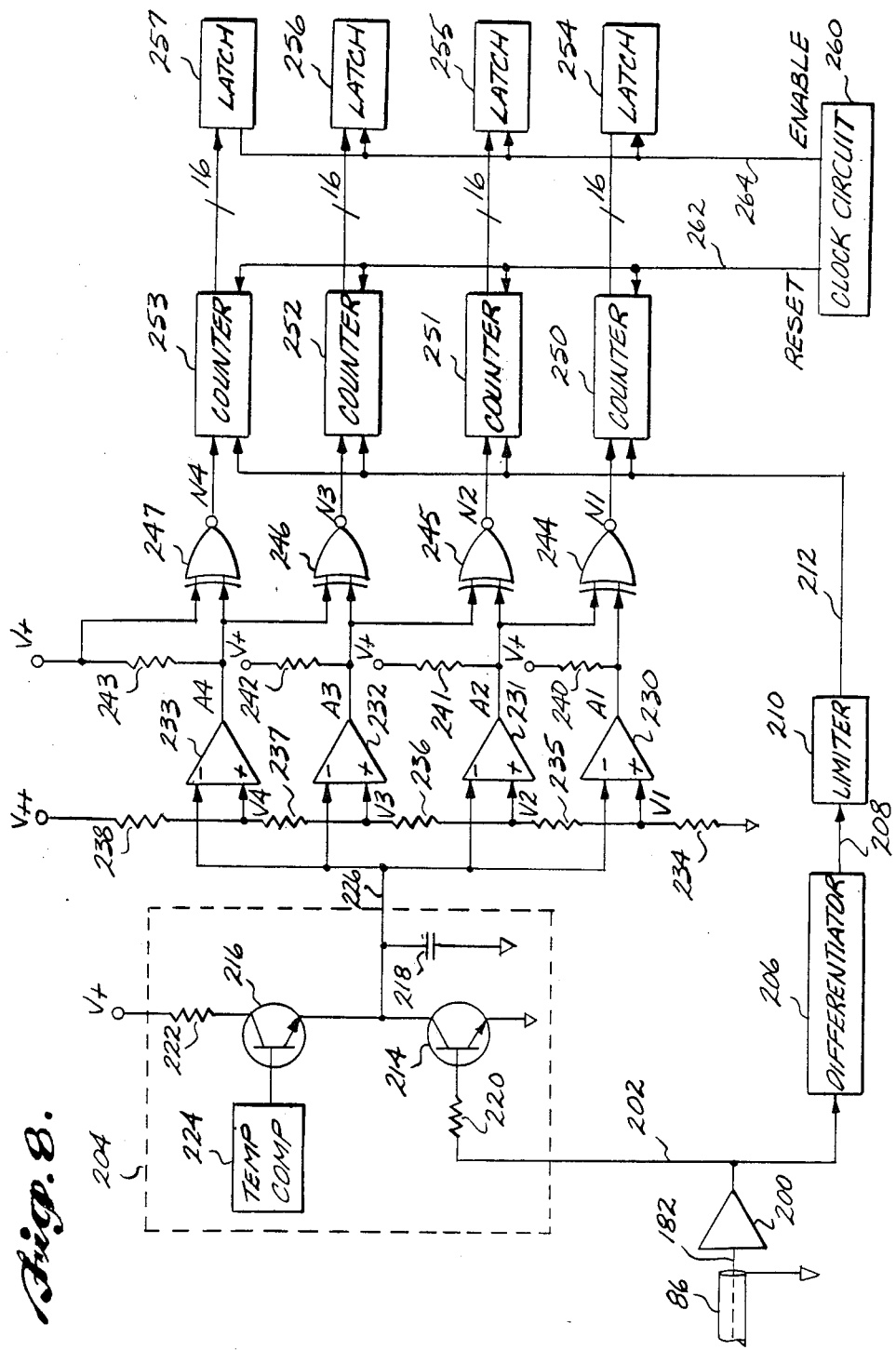
FIG. 8 is a circuit diagram of the detection and counting circuit.

A preferred embodiment of the detection circuit of the present invention is described in FIGS. 8-10. In general, the detection circuit analyzes the pulses produced by the photodiode and preamplifier when the focal spot sweeps past a particle in the fluent medium, or when a particle flows through the focal spot. The illustrated detection circuit classifies the particles into four size categories, counts the particles in each size category, and discriminates against particles that produce pulses with rise times above (i.e., slower than) a predetermined threshold. Any number of size categories may of course be used. The amplified signal from photodetector 106 is received by the detection circuit via line 182 of coaxial cable 86. The signal on line 182 is input to high gain amplifier 200, amplifier 200 preferably having a slew rate on the order of 70 volts/microsecond. The high slew rate of amplifier 200 permits it to track changes in the level of the signal on line 182 without modifying or degrading the signal rise time. The output of amplifier 200 on line 202 is input to ramp circuit 204 and differentiator 206. Typical signals on lines 182 and 202 are illustrated in FIGS. 9A and 9B respectively. Amplifier 200 is biased such that with no input signal, the amplifier output is high, while a positive-going input signal drives the amplifier low. FIGS. 9A and 9B illustrate that amplifier 200 effectively removes noise from the input signal by digitizing the signal, and further illustrates that the rate at which the signal on line 202 changes state is a function of the rise time of the input signal on line 182. Where the context permits, use of the phrase "rise time" herein should be understood to include both the rise time and the fall time of a signal.

Differentiator 206 produces an output signal on line 208 that has an amplitude corresponding to the first derivative of the signal on line 202. The differentiated signal on line 208 is input to limiter 210. Limiter 210 clips the signal on line 208, so as to limit it to +5.5 volts in a positive direction and −0.5 volts in a nagative direction, and produces a clipped and differentiated output signal on line 212 that is illustrated in FIG. 9C. The negative-going portions of the signal on line 202 produce small negative pulses on line 212 due to the action limiter 210. However the positive-going portions of the signal on line 202 produce positive pulses on line 212 that up to 5.5 volts have amplitudes proportional to the rise times of the input signal on line 202, and to the fall times of the signal on line 182 (FIG. 9A). The function of the signal on line 212 is described in greater detail below.

Ramp circuit 204 comprises transistors 214 and 216, capacitor 218, resistors 220 and 222, and temperature compensation circuit 224. Transistors 214 and 216 are connected in series between positive voltage supply $V_+$ and ground. The signal on line 202 is input to the base of transistor 214 via resistor 220. The collector of transistor 214 is connected to capacitor 218, and also forms the output of ramp circuit 204 on line 226. When the signal on line 202 is high, transistor 214 conducts and maintains capacitor 218 in a discharged state. The voltage on line 226 is therefore low at this time. However, when the voltage on line 202 goes negative, transistor 214 stops conducting, and capacitor 218 charges via transistor 216 and 222. The resulting ramp signal on line 226 is shown in FIG. 9D. The rate of charging of capacitor 218 depends upon the voltage provided by temperature compensation circuit 224 at the base of transistor 216. The temperature compensation circuit may therefore be adapted to provide a constant charging rate over the operating temperature of the detection circuit.

The ramp signal on line 226 (FIG. 9D) and the limited derivative signal on line 212 (FIG. 9C) are used to control the operation of a counting circuit that comprises operational amplifiers 230-233, exclusive NOR gates 244-247, counters 250-253, latches 254-257 and clock circuit 260. The ramp signal on line 226 is connected to the inverting input of each of operational amplifiers 230-233. The noninverting inputs of the operational amplifiers are connected to a resistance ladder comprising resistors 234-238 connected between positive voltage supply $V_{++}$ (e.g., 12 volts) and ground, the resistance ladder providing voltages V1 through V4 as shown in FIG. 8. The outputs of operational amplifiers 230-233 (A1-A4) are connected to positive voltage supply $V_+$ (e.g., 5 volts) through resistors 240-243 respectively, and to one of the inputs of exclusive NOR gates 244-247 respectively. The second inputs of the exclusive NOR gates are derived as shown from the outputs of the adjacent operational amplifiers, with the second input of exclusive NOR gate 247 being tied to positive voltage supply $V_{30}$. The outputs of exclusive NOR gates 244-247 (N1-N4) are input to counters 250-253 respectively. Each counter is a 16-bit counter, and the outputs of the counters may be transferred to latches 254-257 by appropriate reset and enable signals provided by clock circuit 260 on lines 262 and 264 respectively.

The operation of the counting circuit illustrated in FIG. 8 can be illustrated with reference to the signal diagram of FIG. 9 and the logic diagram set forth in FIG. 10. In FIG. 10, the columns labeled A1-A4 represent the outputs of amplifiers 230-233 respectively, with 1 standing for a high output voltage and 0 standing for a low output voltage. Similarly, the columns labeled N1-N4 correspond to the outputs of exclusive NOR gates 244-247 respectively. Referring to FIG. 9D, voltage ramp 270 begins when the signal on line 202 (FIG. 9B) goes low and capacitor 218 begins to charge. Initially, the voltage on line 226 is lower than all of the voltages (V1 through V4) provided at the noninverting inputs of amplifiers 230-233. Thus, the outputs A1-A4 of all amplifiers are high, as reflected in the first row of FIG. 10. Similarly, each exclusive NOR gate 244-247 has high signals at both of its inputs, and the outputs of all of the exclusive NOR gates N1-N4 are high, again as indicated in the first row of FIG. 10. As the voltage on line 226 rises, a point is reached on ramp 270, at time $t_1$, at which the voltage on line 226 exceeds the voltage V1 at the noninverting input of amplifier 230. The output of amplifier 230 (A1) therefore goes low, and as a result the output of exclusive NOR gate 244 (N1) also goes low, as illustrated in the second row of FIG. 10. At time $t_2$, the voltage on line 226 exceeds the voltage V2 at the noninverting input of amplifier 231. The output of amplifier 231 (A2) therefore goes low, forcing the output of exclusive NOR gate 245 (N2) to go low and the output of exclusive NOR gate 244 (N1) to go high, as illustrated in the third row of FIG. 10. Continued increase of the voltage on line 226 (not illustrated in FIG. 9D) would result in the signals in rows 4 and 5 of FIG. 10, when ramp 270 exceeds voltages V3 and V4 respectively.

Voltage ramp 270 continues until the signal on line 202 (FIG. 9B) goes high, a high signal on line 202 resulting in the rapid discharge of capacitor 218 through transistor 214. The positive-going signal on line 202 also results in a positive voltage pulse on line 212 (FIG. 9C). The signal on line 212 is connected to the enable input of each of counters 250-253. These counters are adapted to respond to a negative-going enable pulse, provided that the enable pulse voltage was initially greater than 4.5 volts. Thus, in the case of pulse 272 (FIG. 9C), the pulse height is initially above the 4.5 volt threshold, and as a result, the negative-going edge of pulse 272 enables counters 250-253 to receive the signals supplied by exclusive NOR gates 244-247 respectively. Because signals N1, N3 and N4 are high when enable pulse 272 occurs, counters 250, 252 and 253 do not register any counts in response to the enable pulse. However, a count is registered by counter 251 due to the low N2 signal from exclusive NOR gate 245. The N2 signal is illustrated in FIG. 9E. Because of the longer signal path between line 202 and the output of exclusive NOR gate 245, the N2 signal remains low for a short period of time d after the occurrence of pulse 272, thus ensuring that counter 251 registers a count.

After counters 250, 253 have been permitted to accumulate counts for a predetermined period of time, the contents of the counters may be transferred to latches 254-257 by means of an enable signal on line 264. The counters are then reset to zero by a reset signal on line 262, and the process is repeated. Thus at the time that the counter contents are transferred, each latch contains a number corresponding to the number of particles counted in a given size range, the size ranges being defined by voltages V1-V4. The latches may be used to drive display devices, or to transfer the count data to a data storage system or to a process control system.

An important aspect of the present invention is that particles that pass through the light beam too far from the focal spot are not counted. Discrimination against such particles is provided by requiring that enable pulse 272 exceed a predetermined level, for example 2.5 volts. FIG. 9A illustrates pulse 274 resulting from a particle that partially occluded the light beam but that was not contained in the volume through which the focal spot was scanned. As illustrated in FIG. 9C, the slow rise time of pulse 274 results in enable pulse 276 that has an amplitude less than the 2.5 volt threshold. Pulse 274 is therefore ineffective to enable counters 250-253. Consequently, no count is registered for pulse 274, and the required screening of out-of-focus particles is accomplished. It is important to note that the high gain of amplifier 200 coupled with the rise time discrimination provided by differentiator 206 provides a detection circuit that does not depend upon the amplitude of the pulses from the photodiode and preamplifier, but rather on their rise times. The rise time sensitivity of the detection circuit is determined by the time constant of differentiator 206. If the differentiator is implemented by a simple RC circuit, suitable values for the resistor and capacitor are 33 picofarads and 2.2 kilohms, respectively, giving a time constant of 73 nanoseconds. If amplifier 200 has a slew rate of 70 volts/microseconds, the amplifier output will go from +10 volts to −10 volts in about 285 nanoseconds, a change that is comparable to charging the differentiator capacitor to 5 volts in 75 nanoseconds. Thus, the detection circuit counts only those pulses that are fast enough to drive amplifier near its maximum slew rate.

It should be noted that the system described above may be modified to use any number of size categories, and that digital signal processing methods may be used to obtain the rise time and pulse length values. High-speed microprocessing circuits may be used to provide distinct length, amplitude and rise time values for each pulse received, allowing a continuous distribution of all particle sizes to be obtained, rather than a fixed number of size categories.

For some applications, the fluent medium containing the particles to be analyzed will flow at a continuous rate past the point at which the particle sizes and concentrations are to be measured. In such a case, it may not be necessary to scan the focal spot, and particle analysis can proceed by means of a fixed probe and focal spot past which the fluent medium flows. In some cases, the flow rate of the fluent medium will be fixed, in which case such fixed rate can be taken into account in the calibration of the detection circuit. However, when the flow rate of the fluent medium is variable, and where it is desired to determine particle size as well as particle count, then it will generally be necessary to either utilize a flow regulation device to produce a fixed rate of flow past the probe, or to measure the flow rate and take the measured flow rate into account in the detection circuit. The latter situation is illustrated in FIG. 11. In this figure, probe 280 is used to measure particle sizes and numbers in pipe 282 through which fluent medium 283 is flowing in the direction indicated by the arrows. Flow meter 284 is interposed in pipe 282, and produces a flow rate signal on line 292. The system shown in FIG. 11 further includes detection circuit 286 and display 288. The detection circuit receives the signal provided by probe 280 on line 290, and is also connected to receive the flow signal on line 292. The detection circuit may be similar to the circuit shown in FIG.

8. In such a case, the detection circuit would utilize the flow signal on line 292 to alter the time constant of differentiator 206, and also to modify the slope of the ramp produced by ramp circuit 204. The resulting particle sizes and counts could then be displayed by display 288.

In the case where it is not desired to utilize a flow meter, a mechanism may be utilized to produce a constant flow of the fluent medium past the probe. In the case of powdered materials carried in gas, the mechanism may simply comprise a venturi pipe adjacent to the optical window, with air driven dry-air jets that blow the particles past the window. In general, where focal spot scanning is not used, it will be necessary that the flow velocity of the fluent medium be high enough to provide the required counting rates.

The present invention is capable of producing accurate measurements of particle size over a very wide range of particle concentrations, i.e., from 0.01 percent to greater than 20 percent by volume. However, the distance from the window to the focal spot is important to the accuracy of the system. If the focal spot is too far inside the fluent medium, then the particles between the window and the spot may collectively scatter too much of the beam, leaving little of the light energy to be focused (as in the transmission geometries). If the focal point is too close to the window, then the probability of the beam illuminating a particle becomes small, slowing the acquisition of data to unacceptable levels.

It has been discovered that the optimum accuracy in the counting and sizing of particles is achieved by adjusting the distance from the window to the focal spot such that the integrated amplitude is maximized. The integrated amplitude is the average amplitude of the signal on line 182 of FIG. 8. Thus, with reference to FIG. 9A, the integrated amplitude is the integrated average, over all of the pulses appearing on line 182, of the pulse amplitude times the pulse width. The signal on line 182 can be sent to a suitable integrated amplitude circuit, described below, which can produce an indication or signal proportional to the integrated amplitude. Referring to FIG. 1, such a signal can be used with a suitable servo loop to control the stepper motor 80/positioner 76 to automatically adjust the position of the optical assembly 50, and thus the distance between the focal spot and the window, so that the maximum integrated amplitude is achieved. Alternatively, an indication of the integrated amplitude may be used to manually adjust the position of the focal spot.

Figure 12:
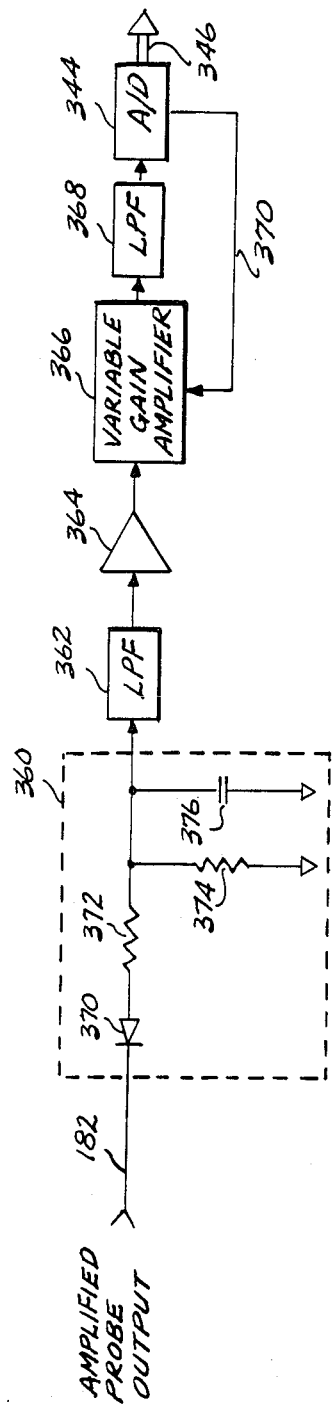
FIG. 12 is a block diagram of an integrated pulse amplitude circuit.

A suitable embodiment for an integrated amplitude circuit is shown in FIG. 12. The integrated amplitude circuit comprises interface circuit 360, low pass filter 362, amplifier 364, variable gain amplifier 366 and low pass filter 368. The preamplified probe output signal on line 182 (FIG. 8) is conveyed to interface circuit 360. The interface circuit comprises diode 370, resistors 372 and 374, and capacitor 376. The interface circuit converts the probe output signal into a properly balanced DC output. The signal produced by the interface circuit is filtered by low pass filter 372, amplified by amplifier 364, and then input to variable gain amplifier 366. The output of the variable gain amplifier passes through a second low pass filter 368, and is then input to A/D 344. A/D 344 controls the gain of amplifier 366 via a feedback signal on line 370, in a manner well known to those skilled in the art, in order to maximize dynamic range. The digital integrated amplitude signal produced by A/D 344 on bus 346 is then input to a servo system, as described above, to control the position of the focal spot.

In many applications there will be a "halo" of light surrounding the focal spot in the fluent medium, caused by secondary and higher order light scattering from particles in the vicinity of the focal spot. Referring to the Lambert-Beer law of light propagation through a fluent medium with suspended particles, the light intensity $I_t$ at distance x from the light source is given by:

$$I_t = I_o e^{-nCkx} \qquad (1)$$

where $I_o$ is the intensity at the source, n is the number of particles, C is the optical cross section of the particles, and k is the absorption coefficient. In the case of backscattered light, the distance x from the source will be different for off-axis detection points, i.e., for light from the halo surrounding the focal spot. The light received by such detectors is then proportional to the product nCk in the equation (1) above. Since k is constant for a given material and C is directly related to the size of the particles, n can be determined and used as a measure of volumetric concentration. Photodiode 108 in FIG. 3 measures the light scattered from areas not included in focal spot 84, and so measures light from the "halo" that has traveled a different distance from the source as has the light received by photodiode 106 from the focal spot. Thus the ratio of the signals from 108 and 106 is a measure of the number n of the particles in the fluent medium.

FIG. 13 illustrates an embodiment in which a common optical path is used for the illumination and backscattered light. The embodiment of FIG. 13 includes laser diode 380, collimating lens 384, beamsplitter 386 and focusing lens 388. The beam emitted from light emitting area 382 of laser diode 380 is collimated by lens 384, passes through beamsplitter 386 and lens 388 into optical conveyance system that may comprise a periscope (optical relay) system, or a fiber optic system. The optical conveyance system projects the illumination light along axis 402, and focuses the illumination light at focal spot 400 in the fluent medium. Light is backscattered from focal spot 400, passes through optical conveyance system 394 to the beamsplitter, and is reflected by the beamsplitter towards lens 404 that focuses the backscattered light onto photodiode 406. It will be noted that the focal plane perpendicular to axis 402 at focal spot 400 will be mapped onto a plane at photodetector 406 normal to the axis 408 of the light beam traveling from the beamsplitter to the photodetector. However, the illumination at photodetector 406 will remain stationary, even as focal point 400 is scanned. In one preferred arrangement, photodetector 406 is a multisectored photodetector adapted to measure not only the scattered light at the center of the beam, but also the off-axis light that is the result of the halo effect.

The configuration of the multisectored photodetector can vary, depending upon what additional information is to be collected. One suitable configuration is shown in FIG. 14. Photodetector 406 consists of two concentric photodetector rings 440 and 442 surrounding centrally located high-speed detector 444 onto which the center of the beam (i.e., the light backscattered by the focal spot) is focused. Centrally located detector 444 is small enough in size to have a highspeed response time, but large enough to capture all of the scattered light from the focal spot 400. The signal from this photodetector is used to analyze the light scattered from individual particles, as described above. Photodetector rings 440 and 442 are larger in size, and pick up light scattered from portions of the halo. The signals produced by these photodetectors are thus largely an average voltage or DC level, and the ratio of the signal produced by photodetector ring 440 to the signal produced by photodetector ring 442 can be used to measure the concentration of particles in the fluent medium.

The present invention provides a particle analysis technique that may be used for on-line applications in process flow and in process vessels. However there are difficulties in using electrical components in areas with high temperatures, and in areas with potentially combustible or explosive environments. For example, laser diodes do not operate in temperatures above about 50° C. Furthermore, in explosive environments, such as environments with combustible solvents, a probe or sensor should be intrinsically safe or at least explosion-proof. An explosion-proof probe is constructed in such a way that it cannot cause or contribute to an explosion, i.e., it is housed in an explosion-proof enclosure. An intrinsically safe probe is a probe that does not use electrical signals or components, and that is otherwise constructed such that it cannot cause or contribute to an explosion. Thus, an intrinsically safe probe need not go through an extensive process to obtain "explosion-proof" certification.

Figure 15:
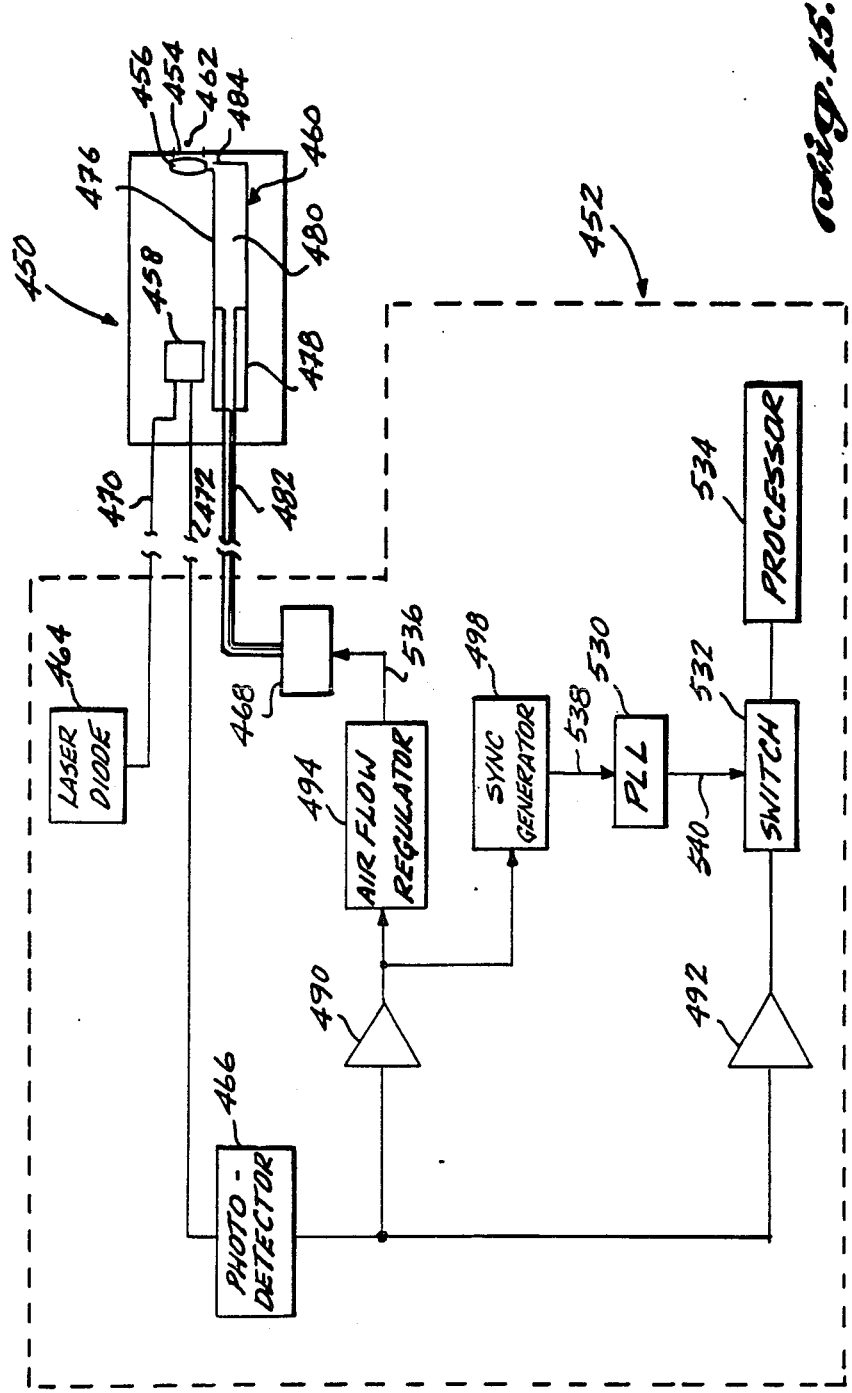
FIG. 15 is a system diagram of an intrinsically safe particle analyzer according to the present invention.

An intrinsically safe particle counting system according to the present invention is shown in FIGS. 15–18. Referring to FIG. 15, this system includes probe 450 and controller 452. Probe 450 is the component of the system that is located at the monitoring site, and is implemented using optical and pneumatic components only. The probe includes window 454, lens 456, optical system 458 and pneumatic oscillator 460. Controller 452 is located remotely with respect to probe 450, and includes laser diode 464, photodetector 466, pneumatic controller 468, and other components described below. Laser diode 464 is coupled to optical system 458 of probe 450 via monomode fiber-optic cable 470, photodetector 466 is coupled to the optical system via multimode fiber-optic cable 472, and pneumatic controller 468 is coupled to the probe via air line 482. Laser diode 464 may include a conventional monomode fiber pigtail that is spliced directly to monomode cable 470. Laser diode 464 produces a single mode optical signal on fiber-optic cable 470 that is received by optical system 458, and formed by the optical system into a beam suitable for transmission to the focal spot 462 via lens 456. In a similar manner, the optical system receives light reflected from the focal spot via lens 456, and couples the light into fiber-optic cable 472 for return to controller 452.

Lens 456 is mounted to one end of leaf spring 476, the other end of the leaf spring being fastened to base 478. Base 478 includes cavity 480, and the leaf spring is positioned such that the leaf spring when undeflected just closes the cavity at lip 484, and such that lens 456 and the end of the leaf spring to which it is attached can vibrate up and down without contacting lip 484. Pressurized air is supplied to cavity 480 via air line 482. In response to the air pressure, leaf spring 476 flexes upward, thereby providing a gap between the end of the leaf spring under lens 456 and lip 484. This gap permits air to escape from the cavity, thus reducing the air pressure in the cavity. Continuation of this process leads to vibration of leaf spring 476 and lens 456, at a resonant frequency that depends on the length and thickness of the leaf spring, and on the mass of lens 456. These parameters may be chosen to produce a suitable scanning frequency, e.g., 400 Hz, with the pressure of air in air line 482 controlling the vibration amplitude. In other suitable pneumatic systems, the air flow or pressure in air line 482 may be used to control the scanning frequency.

The volume of cavity 480 may be varied to increase drive efficiency, and an air flow restrictor may be used to limit the air flow during the upper portions of the vibration of the leaf spring. For some applications, air line 482 will itself serve as a suitable air flow restrictor. It will of course be understood that the pneumatic oscillation system shown in FIG. 15 will not be necessary for those applications in which the particles flow past the probe with suitable velocities.

Figure 16:
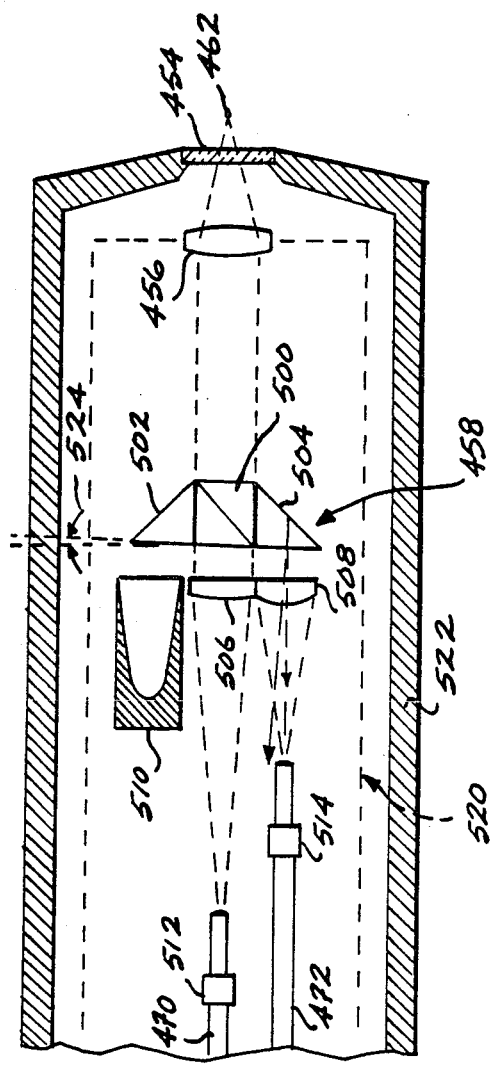
FIG. 16 is a schematic view, partly in cross section, of a portion of the probe of FIG. 15.
Figure 17:
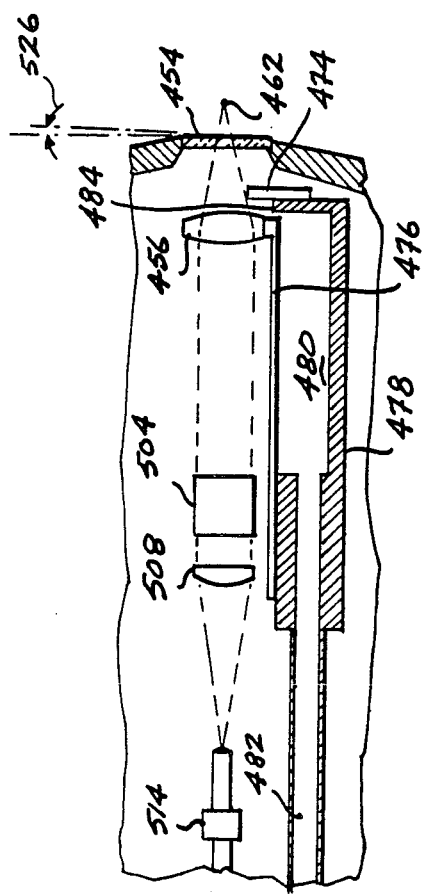
FIG. 17 is a second partial cross-sectional view of the FIG. 15 embodiment.

Further details of probe 450 are shown in FIGS. 16 and 17. As illustrated, optical system 458 includes beamsplitter 500, prisms 502 and 504, lenses 506 and 508, and black body cavity 510. Fiber-optic cable 470 includes termination 512 that is positioned at the focal point of lens 506, such that light exiting from fiber-optic cable 470 strikes and is collimated by lens 506. Termination 514 of fiber-optic cable 472 is positioned at the focal point of lens 508, such that collimated light passing from right to left through lens 508 is focused into fiber-optic cable 472. The optical system, lens 456 and terminations 512 and 514 are mounted within a housing, schematically illustrated by phantom line 520, that in turn is mounted within probe body 522. Preferably, housing 520 is pneumatically movable in a longitudinal direction to adjust the position of focal spot 462 with respect to window 454.

In operation, light from fiber-optic cable 470 is collimated by lens 506 and impinges on beamsplitter 500. A portion of the incident illumination passes through the beamsplitter to lens 456, and is focused onto focal spot 462. The remainder of the incident illumination is reflected by beamsplitter 500 into black body cavity 510 via prism 502. Light returning from focal spot 462 passes via lens 456 and beamsplitter 500 to prism 504 where it is reflected into fiber-optic cable 472 via lens 508. As shown in FIG. 16, beamsplitter 500 and prisms 502 and 504 are offset by a small angle 524 from the optical axis of lens 456, to prevent any reflections from black body cavity 510 from entering fiber-optic cable 472. Similarly, as shown in FIG. 17, window 454 is offset by a small angle 526 from the optical axis of lens 456, to prevent reflections from window 454 from entering fiber-optic cable 472.

The principle of operation of the embodiment of FIGS. 15–18 is that light exiting from the end of single mode fiber-optic cable 470 produces a radiation pattern of spherical waves that appear to be coming from a virtual point source a few microns back from the end face of the fiber. Fiber-optic cable 470 can therefore act as a very compact illumination source, in a manner similar to that for the laser diode itself in previously described embodiments. Thus as with prior embodiments, the embodiment of FIGS. 15–17 is capable of producing focal spot 462 of very small size. Termination 512 is positioned such that the virtual point source is at the exact focal point of lens 506. In principle, it would be possible to use a single fiber-optic cable to transmit light to and from probe 450. However the advantage of the arrangement described above is that reflections caused by splices in the optical path between laser diode 464 and beamsplitter 500 are not coupled into fiber-optic cable 472, and do not produce a DC signal level at photodetector 466. This is an important consideration, because the noise level of a receiving diode goes up with the DC current. Other techniques to minimize the amount of light entering fiber-optic cable 472 from sources other than focal spot 462 are the angular deflections 524 and 526 described above, the use of black body cavity 510, and the use of suitable antireflection coatings on the lenses, beamsplitter and prisms that comprise the optical system.

Use of a multimode cable for fiber-optic cable 472 permits a larger amount of reflected light to be coupled into the fiber-optic cable. The reason for this is that compared to single mode cables, multimode cables have larger core diameters and larger numerical apertures. Furthermore, maintenance of a high degree of spatial coherence is not required for the return optical signal, because of the comparatively large receiving area of photodetector 466. The focal length selected for lens 508 is a tradeoff between competing considerations. A diffraction limited lens of long focal length will produce a larger focal spot than a lens having a short focal length with the same aperture. However, only that portion of the light from lens 508 that falls within the numerical aperture of fiber-optic cable 472 will be coupled into the fiber-optic cable. Thus if lens 508 has a short focal length, it will produce a smaller beam spot at the end of fiber-optic cable 472, but some of the light may be outside of the numerical aperture of the fiber-optic cable. If lens 508 has a long focal length, then it will produce a larger beam spot at the end of fiber-optic cable 472, and a portion of the beam spot may fall on the cladding rather than on the core of the fiber-optic cable. In practice, focal lengths in the range of 10–25 millimeters have been found most suitable.

In addition to the laser diode 464, photodetector 466 and pneumatic controller 468, controller 452 includes amplifiers 490 and 492, airflow regulator 494, sync generator 498, phase lock loop 530, switch 532 and processor 534. Amplifier 490, airflow regulator 494 and pneumatic controller 468 are used to regulate the airflow in air line 482. Amplifier 492 and switch 532 are used to couple the output of photodetector 466 to processor 534. Amplifier 492 may be implemented in a manner identical to the preamplifier shown in FIG. 7, and processor 534 may be similar or identical to the processor shown in FIG. 8. The purpose of sync generator 498, phase lock loop 530 and switch 532, and the operation of the airflow control path, are described below.

To accurately determine particle size, the speed with which focal spot 462 scans through the fluent medium must be known or suitably estimated. As previously described, this may be accomplished by counting particles only during the relatively constant velocity portions of the oscillation of the focal spot. In particular, taking the focal spot motion to be represented by a sine wave, the detection signal may only be processed during those portions of each oscillation in which the phase is in the range 315°–45° and 135°–225°. With the previously described embodiments in which the focal spot oscillation was produced by applying a suitable electrical control signal, synchronizing the focal spot oscillation to the particle counting operation is straightforward. However, in the embodiment of FIGS. 15–17, means must be provided to synchronize the operations of processor 534 to the oscillations produced by pneumatic oscillator 460.

To achieve such synchronization, a small reflector 474 (FIG. 17) is positioned adjacent to lip 484 of base 478. Reflector 474 is positioned such that during the downward excursion of lens 456, the reflector intercepts and reflects a portion of the light passing through lens 456. The reflector is selected such that these reflections produce optical pulses that are significantly larger than the pulses produced by individual particles in the fluent medium. As a result, as the amplitude of vibration of lens 456 increases, the amplitudes of the pulses produced by reflector 474 also increase. These pulses are converted to electrical pulses by photodetector 466, and the corresponding electrical pulses are amplified by amplifier 490 and input to airflow regulator 494 and sync generator 498. The airflow regulator responds by adjusting the control signal on line 536 to achieve a predetermined oscillation amplitude.

Sync generator 498 receives the signal produced by amplifier 490, and produces a series of sync pulses on line 538 that are input to phase lock loop 530. The sync pulses correspond to the points in time of maximum downward travel of lens 456. By way of example, sync generator 498 may comprise a limiter to screen out the smaller pulses produced by particle reflection, a differentiator to differentiate the reflector pulses produced at the output of the limiter, and a rectifier to rectify the differentiator output pulses, to thereby produce sync pulses having leading edges that exactly correspond to the turn around point in the motion of lens 456. The frequency of the sync signal on line 538 corresponds to the frequency of vibration of lens 456. Phase lock loop 530 locks onto this signal, to produce the square wave (50% duty cycle) signal on line 540 that controls switch 532. The sync pulses on line 538 occur at phase angles of 90°. PLL 530 therefore includes a phase shifting circuit to shift its output on line 540 by 45°. Switch 532 is therefore closed during the appropriate phase ranges (315°–45° and 135°–225°), to synchronize the counting operation to the focal spot oscillation.

Figure 18:
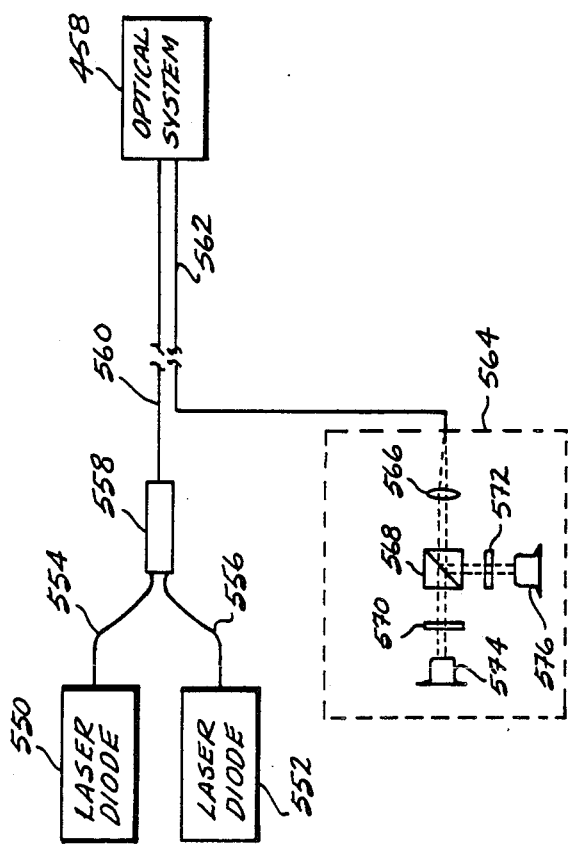
FIG. 18 is a diagram of a dual wavelength system according to the present invention.

In the embodiments described to this point, only the width and rise time of the pulses produced by particles at the focal spot have been utilized. However, the amplitudes of the pulses are a function of the physical characteristics of the particles other than their size, for example, particle shape, refractive index of the particle, color, and chemical make-up. Thus useful additional information can be obtained by analyzing pulse amplitude, and in particular, analyzing the amplitude of pulses reflected at two or more different wavelengths. An embodiment for obtaining such additional information is illustrated in FIG. 18. This embodiment includes laser diodes 550 and 552, coupler 558, and two wavelength detector 564. Laser diodes 550 and 552 produce light at two different wavelengths on single mode fiber optic cables 554 and 556, respectively, and this light is combined by coupler 558 onto single mode fiber optic cable 560. Suitable single mode fiber optic couplers include those in the 945 series available from Amphenol. As in the previous embodiment, the optical signal on single mode cable 560 is input to optical system 458, which in turn produces a return signal on multimode cable 562.

Detector 564 includes collimating lens 566, beamsplitter 568, interference filters 570 and 572, and photodetectors 574 and 576. Lens 566 collimates the light exiting from multimode fiber optic cable 562, and the collimated light is divided by beamsplitter 568 into first and second beams. The first beam is passed through interference filter 570 that passes only light from laser diode 550 to photodetector 574. The second beam produced by the beamsplitter passes through interference filter 572 that passes only that light produced by laser diode 552 to photodetector 576. Thus each photodetector measures only the backscattered light in a particular wavelength range. By taking the sum and difference of the light from the two photodetectors at the same time, one can gain valuable additional analytical information about the specific particles at the focal spot.

While the preferred embodiments of the invention have been illustrated and described, variations will be apparent to those skilled in the art. Accordingly, the invention is not limited to the described embodiments, and the scope of the invention is to be determined by reference to the following claims.

The embodiments of the invention in which an exclusive property or privilege is claimed are defined as follows:

1. An apparatus for analyzing particles contained in a fluent medium, the apparatus comprising:
   a body including a window;
   illumination means mounted to the body, the illumination means comprising an optical source and an optical system for receiving light from the optical source and focusing the light at a focal spot adjacent to the window in the fluent medium, the illumination means including means for adjusting the distance between the focal spot and the window;
   photodetector means for detecting pulses of light resulting from the backscattering of light by particles in the focal spot, and for producing a corresponding electrical signal; and
   detection means connected to receive the electrical signal, the detection means including size measurement means for measuring the length of time that individual particles are in the focal spot and for thereby providing an indication corresponding to the size of particles in the fluent medium, the detection means further including means for producing an integrated amplitude signal having a magnitude corresponding to the average amplitude of the electrical signal, whereby said distance may be adjusted based upon the integrated amplitude signal.

2. The apparatus of claim 1, wherein the optical source comprises a laser diode having a light emitting area, wherein the optical system focuses the light from the laser diode such that the size of the focal spot is approximately equal to the size of the light emitting area.

3. The apparatus of claim 1, wherein the photodetector means includes means for producing an electric signal comprising a series of electrical pulses corresponding to the pulses of light, and wherein the detection means comprises counting means for counting the electrical pulses and discrimination means for preventing the counting of an electrical pulse that has a rise time above a predetermined threshold.

4. The apparatus of claim 1, wherein the illumination means includes means for varying the position of the focal spot with respect to the body in a direction parallel to the window.

5. The apparatus of claim 1, wherein the illumination means includes means for adjusting the distance between the focal spot and the window such that the integrated amplitude signal is at a maximum.

6. The apparatus of claim 1, wherein the optical system comprises a beamsplitter and optical conveyance means for conveying light along a path from the beamsplitter and for focusing the light at the focal spot, and for receiving light backscattered at the focal spot and returning the backscattered light to the beamsplitter, the photodetector means being positioned to receive backscattered light from the beamsplitter.

7. The apparatus of claim 1, wherein the photodetector means includes means for producing an electric signal comprising a series of electrical pulses corresponding to the pulses of light, and wherein the detection means includes means for separately counting the electrical pulses in a plurality of ranges of pulse length, whereby the numbers of particles in a plurality of size ranges are determined.

8. The apparatus of claim 7, wherein the detection means comprises a plurality of first counters, each first counter being associated with a particular range of pulse lengths, means responsive to each electrical pulse for determining the pulse length and providing a signal to a selected first counter in whose range the pulse length falls, and enable means for providing an enable signal operative to enable the selected first counter to increment its count, the enable means providing the enable signal if the rise or fall time of a pulse is below a predetermined threshold.

9. The apparatus of claim 1, wherein the illumination means comprises a monomode fiber optic cable having first and second ends, and a laser diode including means for coupling light from the laser diode into the first end of the monomode fiber optic cable, the optical system being positioned to receive light from the second end of the monomode fiber optic cable.

10. The apparatus of claim 9, wherein the photodetector means comprises a photodetector and a return fiber optic cable having a first end positioned to receive light backscattered by particles at the focal spot from the optical system, and a second end coupled to the photodetector, and wherein the apparatus is physically divided into a probe and a controller, the probe comprising the optical system and the controller comprising the laser diode, the photodetector and the detection means, whereby an intrinsically safe probe having no electrical components may be provided.

11. The apparatus of claim 10, wherein the probe comprises the body to which the optical system is mounted, wherein the optical system includes pneumatic scanning means for varying the position of the focal spot with respect to the body at a scanning frequency such that the focal spot is scanned through the fluent medium with respect to the body.

12. The apparatus of claim 11, wherein the probe includes reflector means for producing an optical timing signal in the fiber optic return cable having a frequency that varies with the scanning frequency, such that the photodetector produces a corresponding electrical timing signal, and wherein the detection means include means for receiving the electrical timing signal and for providing an indication corresponding to the number of particles in the fluent medium only from predetermined focal spot positions.

13. The apparatus of claim 9, wherein the illumination means comprises a monomode fiber optic cable having first and second ends, first and second laser diodes adapted to emit light at respective first and second wavelengths, and means for coupling light from the laser diodes into the first end of the monomode fiber optic cable, and wherein the photodetector means comprises first and second photodetectors, a return fiber optic cable having a first end positioned to receive light backscattered by particles at the focal spot from the optical system, and means for spectrally dividing the light received from the second end of the return fiber optic cable such that light at the first wavelength band is substantially coupled only to the first photodetector, and light at the second wavelength is substantially coupled only to the second photodetector.

14. The apparatus of claim 1, wherein the window comprises synthetic sapphire mounted in a titanium holder.

15. A method for analyzing particles contained in a fluent medium, the method comprising:
producing illumination light;
projecting the light through a window into the fluent medium such that the light is focused at a focal spot adjacent to the window in the fluent medium;
detecting pulses of light resulting from the backscattering of light by particles at the focal spot, and producing a corresponding electrical signal;
processing the electrical signal to produce an indication corresponding to the length of time that individual particles are in the focal spot for thereby providing an indication corresponding to the size of particles in the fluent medium;
producing an integrated amplitude signal having a magnitude corresponding to the average amplitude of the electrical signal; and
varying the distance between the focal spot and the window such that the integrated amplitude signal is at a maximum.

16. The method of claim 15, wherein the illumination light is focused to a focal spot having a size approximately equal to the size of the source of illumination light.

17. The method of claim 15, wherein the step of detecting includes producing an electrical signal comprising a series of electrical pulses corresponding to the pulses of light, and wherein the processing step includes counting the electrical pulses, and preventing the counting of an electrical pulse that has a rise time above a predetermined threshold.

18. The method of claim 15, wherein the step of detecting includes producing an electrical signal comprising a series of electrical pulses corresponding to the pulses of light, and wherein the processing step comprises separately counting the electrical pulses in a plurality of ranges of pulse length, to thereby determine the number of particles in a plurality of size ranges.

19. The method of claim 15, comprising the further step of varying the position of the focal spot parallel to the window to scan the focal spot through the fluent medium.

20. An apparatus for analyzing particles contained in a fluent medium, the apparatus comprising:
illumination means comprising an optical source and an optical system for receiving light from the optical source and focusing the light at a focal spot in the fluent medium;
photodetector means for detecting pulses of light resulting from the backscattering of light by particles in the focal spot, and for producing a corresponding electrical signal comprising a corresponding series of electrical pulses; and
detection means connected to receive the electrical signal, the detection means comprising counting means for counting the electrical pulses and discrimination means for preventing the counting of an electrical pulse that has a rise time above a predetermined threshold.

21. The apparatus of claim 20, wherein the detection means further includes means for separately counting the electrical pulses in a plurality of ranges of pulse length, whereby the numbers of particles in a plurality of size ranges are determined.

22. The apparatus of claim 21, wherein the detection means further includes size measurement means for measuring the length of time that individual particles are in the focal spot and for thereby providing an indication corresponding to the size of particles in the fluent medium.

23. The apparatus of claim 20, further comprising a body to which the illumination means is mounted, the body including a window, and wherein the illumination means positions the focal spot outside the body adjacent to the window.

24. The apparatus of claim 23, wherein the illumination means includes means for varying the position of the focal spot with respect to the body in a direction parallel to the window.

25. The apparatus of claim 23, wherein the detection means further includes means for producing an integrated amplitude signal having a magnitude corresponding to the average amplitude of the electrical signal, and wherein the illumination means includes means for adjusting the distance between the focal spot and the window such that the integrated amplitude signal is at a maximum.

26. A method for analyzing particles contained in a fluent medium, the method comprising:
producing illumination light;
focusing the illumination light at a focal spot in the fluent medium;
detecting pulses of light resulting from the backscattering of light by particles at the focal spot, and producing an electrical signal comprising a corresponding series of electrical pulses; and
processing the electrical signal, the processing step including counting the electrical pulses, and preventing the counting of an electrical pulse that has a rise time above a predetermined threshold.

27. The method of claim 26, wherein the processing step includes producing an integrated amplitude signal having a magnitude corresponding to the average amplitude of the electrical signal, and wherein the method comprises the further step of varying the position of the focal spot along a longitudinal axis of the illumination light such that the integrated amplitude signal is at a maximum.

28. The method of claim 26, wherein the processing step comprises separately counting the electrical pulses in a plurality of ranges of pulse length, to thereby determine the number of particles in a plurality of size ranges.

29. The method of claim 26, comprising the further step of varying the position of the focal spot to scan the focal spot through the fluent medium.

* * * * *